(12) United States Patent
Davies et al.

(10) Patent No.: US 7,887,691 B2
(45) Date of Patent: Feb. 15, 2011

(54) ARRAYS OF ELECTRODES COATED WITH MOLECULES AND THEIR PRODUCTION

(75) Inventors: Alexander Giles Davies, Leeds (GB); Christoph Walti, Leeds (GB); Anton Peter Jacob Middelberg, Brookfield (AU); Michael Pepper, Cambridge (GB); Rene Wirtz, Dresden (DE)

(73) Assignee: Cambridge University Technical Services Limited, Cambridge (GB)

( * ) Notice: Subject to any disclaimer, the term of this patent is extended or adjusted under 35 U.S.C. 154(b) by 954 days.

(21) Appl. No.: 10/530,694

(22) PCT Filed: Oct. 9, 2003

(86) PCT No.: PCT/GB03/04368

§ 371 (c)(1),
(2), (4) Date: Dec. 28, 2005

(87) PCT Pub. No.: WO2004/033724

PCT Pub. Date: Apr. 22, 2004

(65) Prior Publication Data

US 2006/0151324 A1      Jul. 13, 2006

(30) Foreign Application Priority Data

Oct. 10, 2002    (GB)    .................... 0223666.9

(51) Int. Cl.
*C25D 5/02* (2006.01)
(52) U.S. Cl. ...................................... 205/135; 205/118
(58) Field of Classification Search .................. 205/118, 205/122, 135; 204/224 R, 280
See application file for complete search history.

(56) References Cited

U.S. PATENT DOCUMENTS 6,093,302 A    7/2000    Montgomery (Continued)

FOREIGN PATENT DOCUMENTS

WO    WO 99/51778    10/1999

(Continued)

OTHER PUBLICATIONS

Caillat et al. (1999) "Biochips on CMOS: An Active Matrix Address Array for DNA Analysis," *Sensors and Actuators* 61(1-3):154-162.

(Continued)

*Primary Examiner*—Luan V Van
(74) *Attorney, Agent, or Firm*—Greenlee Sullivan P.C.

(57) ABSTRACT

The present invention provides a method of forming coatings of at least two different coating molecules on at least two electrodes, the method comprising: (a) providing an array of at least two individually-addressable electrodes, (b) allowing a layer of a masking molecule to adsorb onto all electrodes, (c) inducing electrochemical desorption of the masking molecule from at least one but not all electrodes to expose a first set of exposed electrodes, (d) allowing a first coating molecule to adsorb onto the first set of exposed electrodes, (e) exposing all electrodes to a masking molecule to allow adsorption of the masking molecule onto all electrodes, (f) inducing electrochemical desorption of masking molecule from a second set of electrodes to expose a second set of exposed electrodes, (g) allowing a second coating molecule to adsorb onto the second set of exposed electrodes.

25 Claims, 2 Drawing Sheets

U.S. PATENT DOCUMENTS 6,355,420 B1 *   3/2002   Chan .............................. 435/6

FOREIGN PATENT DOCUMENTS

WO          WO 03/020415           3/2003

OTHER PUBLICATIONS

Carcenac et al. (2002) "Fabrication of Multiple Nano-Electrodes for Molecular Addressing Using High-Resolution Electron Beam Lithography and Their Replication Using Soft Imprint Lithography," *Microelectronic Eng.* 61-62:657-663.

Mirkin et al. (1996) "A DNA-Based Method for Rationally Assembling Nanoparticles into Macroscopic Materials," *Nature* 382:607-609.

Mirsky, V.M. (2002) "New Electroanalytical Applications of Self-Assembled Monolayers," *Trends Analytical Chem.* 21(6-7):439-450.

Philipp et al. (1999) "Shadow Evaporation Method for Fabrication of Sub 10nm Gaps Between Metal Electrodes," *Microelectron. Eng.* 46:157-160.

Sullivan et al. (1999) "Automated Electrochemical Analysis with Combinatorial Electrode Arrays," *Anal. Chem.* 71(19):4369-4375.

Tender et al. (1996) "Electrochemical Patterning of Self-Assembled Monolayers onto Microscopic Arrays of Gold Electrodes Fabricated by Laser Ablation," *Langmuir* 12:5515-5518.

Wang et al. (2000) "Electrochemically Induced Deposition of Thiol-Based Monolayers onto Closely Spaced Microelectrodes," *Langmuir* 16(25):9687-9689.

Wilhelm et al. (2001) "Patterns of Functional Proteins Found by Local Electrochemical Desorption of Self-Assembled Monolayers," *Electrochimica Acta* 47(1):275-281.

International Search Report for PCT/GB2003/004368 mailed Jan. 30, 2004.

* cited by examiner

ARRAYS OF ELECTRODES COATED WITH MOLECULES AND THEIR PRODUCTION

CROSS-REFERENCE TO RELATED APPLICATIONS

This application is the U.S. National Stage of International Application No. PCT/GB2003/004368, filed Oct. 9, 2003, which claims the benefit of Great Britain Patent Application No. 0223666.9, filed Oct. 10, 2002, which are hereby incorporated by reference in their entireties.

FIELD OF THE INVENTION

The invention relates to methods for production of arrays of a number of different coating molecules by forming coatings on a number of different electrodes. It also relates to arrays of molecules produced by these methods.

BACKGROUND OF THE INVENTION

Among the many challenges facing the development of a molecular-based nanotechnology, the directed assembly of discrete molecular objects, and their controlled integration into macroscopic structures, are fundamental. The selective self-assembly characteristic inherent to certain molecules (for example, the Watson-Crick specific base pairing that occurs between complementary single strands of DNA) is a property that could be exploited to address these challenges. For example, ordered suspensions of gold nanoparticles have been assembled by first functionalizing the nanoparticles with short DNA oligonucleotides and then introducing complementary DNA to tie the individual particles together as the strands hybridise (Mirkin et al, "A DNA-based method for rationally assembling nanoparticles into macroscopic materials", Nature 382, 607-609 (1996)). In principle, this concept could be employed to tackle the integration of nanoscale elements onto a macroscopic substrate, such as an array of metal electrodes. Providing each electrode is functionalized with anchoring oligonucleotides of a unique sequence, the nanoscale elements will assemble appropriately if they are functionalized with the complementary oligonucleotides.

Indeed, the ability to pattern a surface locally with different molecular monolayers in a well-controlled fashion and with a high spatial resolution has importance for molecular electronics and biotechnology applications (including high density DNA expression analysis and genotyping), as well as for nanoengineering.

However, the selective multiple coating of electrode arrays with appropriate anchor molecules has not yet been demonstrated on structures where the electrode separations are sub-micrometre, limiting the applicability of this procedure for nanoscale assembly.

A number of techniques are available for introducing oligonucleotides or other anchor molecules locally onto a surface, but none of these simultaneously meet the requirements of resolution, speed and the ability to coat different electrodes uniquely. Microdrop dispensing systems provide simple approaches for the controlled multiple coating of an electrode array, but are restricted to a spatial resolution of greater than 10 □m. Micromachining and microcontact printing offer spatial resolutions of several hundred nanometres but lack the ability to effect multiple coating. A much higher resolution (a few tens of nanometres) has been achieved by nanografting, but this technique is slow, lacks a straightforward extension to allow multiple coating, and requires complex and expensive infrastructure. Recently, a variant of the nanografting technique, dip-pen nanolithography, has been reported. This technique uses an AFM (atomic force microscope) tip, coated with the anchor molecules, as a pen to draw onto the surface. The resolution of this coating technique is also on the nanometre scale, but a high level of stability and solubility of the anchor molecules is required.

It is known that monolayers of thiol compounds can be formed on a gold surface by immersing the surface in an aqueous solution containing the thiol molecule of interest. The gold-sulphur bond formed during this spontaneous chemisorption process can undergo reductive cleavage at about −1 V versus a Ag/AgCl reference electrode, leading to electrochemical desorption. Compounds having different functionalities can also form monolayers on gold surfaces and undergo electrochemical desorption. Similarly, monolayers of molecules having other functional groups can assemble on other surfaces, from which electrochemical desorption is also possible.

Electrochemical desorption has been applied by Wilhelm et al in "Patterns of functional proteins formed by local electrochemical desorption of self-assembled monolayers", Electrochimica Acta., vol 47, No. 1, 2001/September, pages 275-281. The authors form an alkane thiolate monolayer on a gold electrode and use a scanning electrochemical microscope (SECM) to induce local electrochemical desorption at defined regions of the alkane thiolate monolayer by using an ultramicroelectrode (UME) of 10 μm diameter placed about 5 μm above the macroscopic SAM-covered gold electrode. The exposed regions are then able to chemisorb an ω-functionalised thiol or disulphide such as cystamine. Functional proteins can then be coupled to the amino groups present in the modified regions of the monolayer. Because this method relies on desorption from regions of one large electrode using an UME above the electrode it is subject to resolution restrictions and indeed is restricted to a spatial resolution of around 10 μm. It means that it can be difficult to control the system so that desorption is not induced at areas neighbouring the intended area for desorption.

A different technique is described by Tender et al in "Electrochemical patterning of self-assembled monolayers onto microscopic arrays of gold electrodes fabricated by laser ablation", Langmuir, 1996, 12, 5515-5518. This group describe use of an array of individually-addressable gold microelectrodes. One technique involves adsorption of a monolayer of (1-mercaptoundec-11-yl) hexa(ethylene glycol) ($EG_6SH$) on all electrodes. Electrochemical desorption is then induced from alternating bands of electrodes, by controlling the potential at the electrodes from which desorption is required. Adsorption of a layer of hexadecanethiol ($C_{16}SH$) is then allowed to adsorb onto the thus-exposed bands. Thus, alternating bands of $C_{16}S$ and $EG_6S$ monolayers are obtained. Non specific absorption of BSA-antibody onto the $C_{16}S$ bands is then allowed and BSA binds specifically to the antibody.

It is stated that the extension of electrochemical desorption of SAMs to pattern SAMs of n different ω-substituted alkane thiols onto n individually-addressable microscopic gold elements "should also be straightforward". However, we are not aware of any further publications by this group along these lines. Furthermore, we believe that the suggested sequential stripping of the $EG_6S$ SAM from different elements and exposure to new alkane thiols, using the method described by Tender et al, would result in contamination of previously patterned layers with subsequently introduced alkane thiols.

Therefore it would be desirable to provide a method for the formation of an array of two or more different molecules, the method being capable of giving nanoscale resolution (distance between areas coated with different molecules) and high purity of the individually patterned regions. It would also be desirable to provide such a method which can be carried out conveniently and at high speed.

SUMMARY OF THE INVENTION

According to the invention we provide a method of forming coatings of at least two different coating molecules on at least two electrodes, the method comprising:

(a) providing an array of at least two individually-addressable electrodes,
(b) allowing a layer of a masking molecule to adsorb on to all the electrodes,
(c) inducing electrochemical desorption of the masking molecule from at least one but not all electrodes to expose a first set of exposed electrodes,
(d) allowing a first coating molecule to adsorb onto the first set of exposed electrodes,
(e) exposing all electrodes to a masking molecule to allow adsorption of the masking molecule onto all electrodes,
(f) inducing electrochemical desorption of masking molecule from a second set of electrodes to expose a second set of exposed electrodes,
(g) allowing a second coating molecule to adsorb onto the second set of exposed electrodes.

We find that the process has the advantage of allowing formation of arrays of a large number of different coating molecules coated with high purity at nanoscale resolution. In particular, we find that use of an array of individually-addressable electrodes has significant advantages over the method described by Wilhelm et al (which induces desorption from different regions of a single electrode) that resolution can be greater and effects on regions neighbouring the electrodes can be controlled to avoid unwanted desorption.

Step (e) is particularly important in the invention. This is a reprotection step in which adsorption of a masking molecule is allowed to take place onto all electrodes, including the electrodes provided with a layer of masking molecule and those onto which adsorption of the coating molecule has occurred. We find that this step, not used or suggested by Tender et al, prevents adsorption of subsequent coating molecules onto electrodes already coated by coating molecules in later steps and minimises contamination. This allows the provision of large numbers of highly pure coatings of different coating molecules.

We find that by the invention we can for the first time produce an array of electrodes having nanoscale separation coated with different coating molecules. Therefore in a second aspect we provide an array of at least 3, preferably at least 5, more preferably at least 10 sets of individually-addressable electrodes, each set having adsorbed thereon a different coating molecule, the minimum distance between electrodes being not more than 900 nanometres, preferably not more than 100 nanometres, more preferably not more than 50 nanometres.

DETAILED DESCRIPTION OF THE PREFERRED EMBODIMENTS

Figure 1:
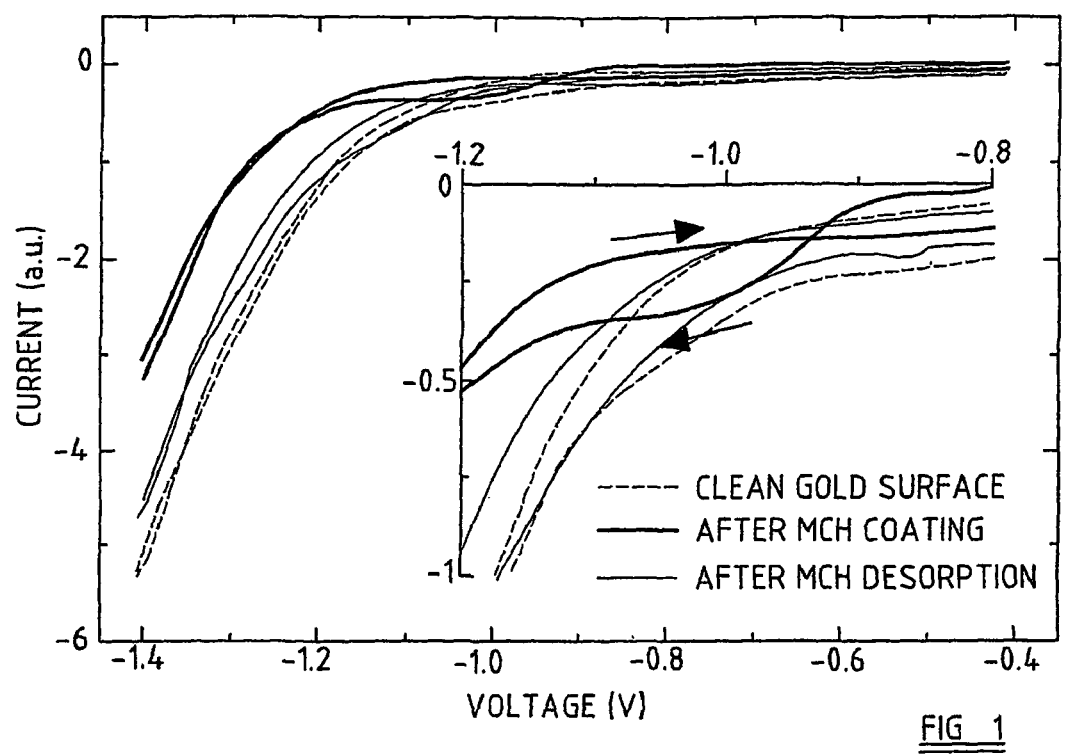
FIG. 1 shows CV traces of clean, coated and exposed electrodes.

The method of the invention requires the use of an array of at least two individually-addressable electrodes. Such arrays are known and can be made in known manner. One method is described below. Preferably the array comprises at least 10, more preferably at least 20, particularly preferably at least 50 individually-addresssable electrodes.

Although the method of the invention is applicable to electrodes on any scale, it is particularly beneficial for providing arrays of small electrodes, particularly of diameter (largest dimension) in the micron range (e.g. below 50 µm), preferably on a nanoscale, namely at nanometre resolution. Thus preferably the electrodes have a diameter of not more than 900 nanometres, preferably not more than 500 nanometres, more preferably not more than 100 nanometres.

A particular benefit of the invention is the fact that it allows coating of closely spaced electrodes. The minimum distance between neighbouring electrodes can be below 80 µm, preferably below 30 µm and even below 10 µm. Preferably the minimum distance between neighbouring electrodes is not more than 900 nanometres, more preferably not more than 500 nanometres, even more preferably not more than 100 nanometres, most preferably not more than 50 nanometres. The method of the invention can even be applied when the separation between electrodes is less than 25 nanometres. This separation preferably applies to the minimum distance between all neighbouring electrodes.

The electrodes are formed of electrically conductive material. Preferably they are metallic but can for instance be non-metallic such as carbon or silicon electrodes. Gold, silver, platinum, copper and aluminium, in particular gold, are preferred.

Generally all electrodes are formed from the same material, although it is possible in the invention that some electrodes are formed from one material and one or more additional sets of electrodes are formed from different materials.

In step (b) of the method a layer of masking molecule is adsorbed onto all electrodes, preferably after cleaning the electrodes in standard manner. One suitable cleaning method is described below.

The masking molecule is adsorbed onto the surface of the electrodes. Thus it must be capable of adsorbing onto a surface formed of the material from which the electrodes are formed. Preferably the molecule contains a functional group capable of forming a bond with the electrode surface so as to form a monolayer of the masking molecule. Of course, the electrodes must be chosen so that the material from which they are formed is such that molecules exist which can form bonds with it.

A variety of molecule types which can form bonds with a variety of surfaces are known. Examples of masking molecules are thiolated molecules which can form bonds with, and hence adsorb onto gold and silver and other metal surfaces, and silicon surfaces. A particularly preferred combination is gold electrodes and a thiolated masking molecule. Suitable thiolated masking molecules are known and include substituted and unsubstituted alkane thiols. Suitable substituents include hydroxyl. Other masking molecules are those having alkyl groups which can absorb onto silicon electrodes.

The masking molecule chosen should be electrochemically active in combination with the material from which the electrode is formed. It should be capable of adsorbing and electrochemically desorbing under convenient conditions, taking into account the nature of the coating molecule also to be used in the method. It should be chosen so that it undergoes electrochemical desorption at a convenient potential, in particular at a potential which is not so high that it results in damage to the coating molecules also used in the method. For instance, preferred masking molecules undergo electrochemical desorption from the chosen electrode at a potential in the range −10V to +10V, preferably −5V to +5V, more preferably −2V to +2V. Masking molecules which undergo electrochemical desorption at a negative potential are preferred.

Generally the masking molecule will have relatively low molecular weight, for instance below 500, in particular below 200 or 150. Smaller masking molecules are preferred as these are more effective at reprotection in the reprotection step (e) discussed further below. They also form a dense monolayer, which is advantageous.

The masking molecule is generally provided in solution, preferably aqueous solution. Concentrations may be chosen as convenient and can range for instance from 0.1 millimolar to 10 millimolar, preferably from 0.5 millimolar upwards.

The electrodes are contacted with the masking molecule for a time appropriate to allow adsorption of the molecule onto the electrode surfaces. The time required will depend upon the precise conditions but is generally not more than 180 mins, preferably not more than 90 mins.

After the adsorption step (b) all electrodes will be provided with a monolayer of the masking molecule.

Step (c) in the method requires inducing electrochemical desorption of the masking molecule from a predetermined set of electrodes. This is carried out in known manner by controlling the potential at the relevant electrodes.

A first set of electrodes is chosen for desorption of the first masking molecule. At least one but not all of the electrodes are treated in this manner. They form the first set of exposed electrodes.

The electrodes from which electrochemical desorption is not required are generally held at open circuit. However, the potential at some or all of these other electrodes can be controlled to counteract any possible effects on them from electrodes from which desorption is required, especially when these are neighbouring electrodes. This is particularly useful when the minimum distance between electrodes is 20 nm or less.

Desorption can be carried out for any appropriate duration to allow all desired molecules to desorb. Preferably desorption time is not more than 300 secs, more preferably not more than 240 secs.

Desorption can be carried out under the influence of AC or DC voltage. If AC voltage is chosen then the amplitude and frequency are chosen so as to ensure that the adsorbed masking molecules are subject to the electrochemical desorption potential for a sufficient period of time to allow electrochemical desorption to occur.

In step (d) a first coating molecule is allowed to adsorb onto the first set of exposed electrodes. This can be a small molecule, for instance of molecular weight not more than 500. However, in this case it preferably is a molecule capable of binding a macromolecule such as a polypeptide after the coating step. For instance it can be an amino-terminated molecule capable of binding a protein.

Preferably however the coating molecule is a macromolecule. Thus it preferably has molecular weight at least 800, preferably at least 1000, more preferably at least 1500, most preferably at least 3000.

Preferred types of macromolecule are oligonucleotides (e.g. 5 to 150 bases). These can be used to form arrays of a large number of different strands of DNA (DNA chips) e.g. for use in gene screening or for use as anchoring nucleotides for inducing directed assembly of nanoscale elements functionalised with complementary oligonucleotides, e.g. for use in molecular electronics.

Alternative macromolecules are polypeptides, including proteins such as enzymes. These can be used, for instance, in biosensor applications. Proteins and oligopeptides can be used in nanoscale assembly applications.

The coating molecule is capable of adsorbing onto the material from which the electrodes are formed. Thus they can be functionalised with a functional group capable of adsorbing. Any suitable functional group can be used provided it is compatible with the electrode material. For instance, thiolated coating molecules are preferred, in particular when the electrodes are gold or silver, particularly gold.

The first coating molecule is generally provided in solution, preferably aqueous solution. Concentration can be chosen as appropriate but is generally in the range 1 to 100 micromolar, preferably 5 to 50 micromolar.

Adsorption times are generally in the ranges given above for adsorption of the first masking molecule.

In some cases it can be preferred to subject oligonucleotide and other coating molecules to an electric field during the adsorption step (d) in order to induce appropriate orientation. It has been shown that DNA molecules experience a dielectrophoretic force and an orientational torque in a non-uniform electric field as a result of the interaction between the induced dipole in the DNA and the electric field. The torque and the dielectrophoretic force are a function of the magnitude and the frequency of the applied electric field. In the invention this effect can be used to assist and accelerate the adsorption process. The molecules are attracted to the electrodes and oriented into the right spatial orientation for adsorption when a suitable electric field is applied. This applied field can be an AC or a DC field. AC field is preferred.

This process can also be utilised during the electrochemical desorption steps. The electric field applied in order to induce orientation can be super imposed onto the voltage applied to induce electrochemical desorption.

In some embodiments it is preferred to allow passive adsorption but in some embodiments it can be preferred to apply an electrochemical potential (AC or DC) to the electrodes in order to accelerate the adsorption process (i.e. active adsorption). Adsorption rates can in some cases be up to two orders of magnitude higher than in passive adsorption, that is adsorption without application of any electrochemical potential. Electrochemical assistance of this type, when used, is preferably applied to step (d), namely the adsorption of the first (and subsequent) coating molecule onto the electrodes, but can also be applied to the adsorption of the masking molecule.

The electrochemical desorption (c) and the adsorption step (d) are preferably carried out sequentially, namely desorption is completed prior to contact of the exposed electrodes with the coating molecule. However, in some applications it can be preferred to induce electrochemical desorption of the masking molecule when the electrodes are in contact with the coating molecules so that the two steps can take place simultaneously.

Step (e) in the method of the invention is the reprotection step. All electrodes are exposed to a second masking molecule so that the second masking molecule can be adsorbed onto all electrodes. This second masking molecule can be selected from any of those discussed above for the masking molecule and preferably is the same molecule as is used in step (b). Conditions for this adsorption step can be selected from those discussed above in connection with step (b).

During this step it is believed that the masking molecule adsorbs onto the just-coated electrodes between the coating molecules. Generally, the monolayer of coating molecules has not completely covered the electrodes and the monolayer of coating molecules is somewhat discontinuous. The masking molecules thus protect these electrodes and prevent adsorption of different coating molecules onto these electrodes in future steps.

Steps (f) and (g) essentially consist of repeating steps (c) and (d) for a second set of electrodes and a second coating molecule.

The second coating molecule is preferably selected from the same class of molecules as discussed above for the first coating molecule. It is a different molecule from the first coating molecule.

Steps (c) to (e) are then repeated as desired to form further sets of exposed electrodes, and expose these sets to further masking molecule.

Thus the method of the invention can be used to provide any number of sets of exposed electrodes carrying the same number of different coating molecules. In some cases an array can be produced in which every electrode is coated with a different coating molecule.

Examples

A series of opposing gold electrodes of sub-50 nm-separation was fabricated on a Si/SiO$_2$ wafer using known UV lithography/lift off techniques as described below. The wafer was cleaned by washing in 'piranha etch' (30% H$_2$O$_2$, 70% H$_2$SO$_4$) for 1 hour, and then thoroughly rinsed in deionised water, ethanol, and again in deionised water. The entire electrode array was then coated with a protective molecular monolayer of 6-mercapto-1-hexanol (MCH) by immersing the wafer in a 1 mM aqueous solution of MCH for 60 min. FIG. 1 compares the CV trace of a coated electrode (solid line) with that of a clean electrode prior to coating (dashed line). A reductive desorption feature observed at around −1 V for the coated electrode indicates the removal of the MCH monolayer. All electrochemical measurements were performed in 100 mM phosphate buffer at pH 10 using a standard three electrode setup at a rate of 62 mV/s. A high purity platinum wire was used as the counter electrode. All electrochemical potentials are reported vs. a Ag/AgCl reference electrode.

To obtain complete desorption of the MCH monolayer from a particular electrode, an electrochemical potential of −1.4 V vs. Ag/AgCl was applied to the electrode for two minutes while keeping all other electrodes at open circuit. FIG. 1 shows the CV trace after this procedure (dotted line), which, when compared with the trace for the clean surface, demonstrates that the monolayer on this particular electrode was removed. The other electrodes, which were kept at open circuit during the desorption step, were not affected and their CV traces remained similar to the solid line in FIG. 1. (not shown). The large increase in current observed in all traces below −1.2 V is associated with hydrogen evolution.

Figure 2:
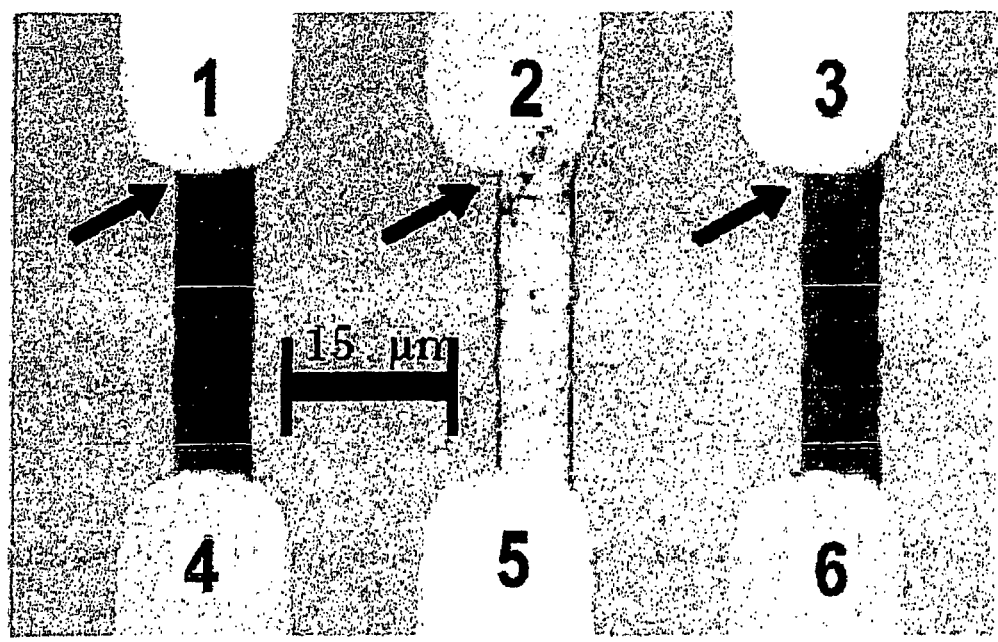
FIG. 2 shows an electrode array from which a masking molecule has been selectively desorbed.

In order to demonstrate that the MCH monolayer can act as a molecular mask, FIG. 2 shows an electrode array from which the MCH was selectively desorbed from electrodes numbered 2, 4 and 6. Thiofated oligonucleotides X of sequence CAGGATGGCGAACAACAAGA-thiol (the thiol is connected to the oligonucleotide via a carbon C$_6$-linker) were dissolved in 10 mM tris(hydroxymethyl)aminomethane, 1 mM EDTA and 1 M NaCl solution of pH 8 to a final concentration of 10 W. The array; with the MCH molecular mask now covering only electrodes 1, 3 and 5, was then immersed in this aqueous solution for 60 min to allow the oligonucleotides to chemisorb to the exposed electrodes.

Figure 3:
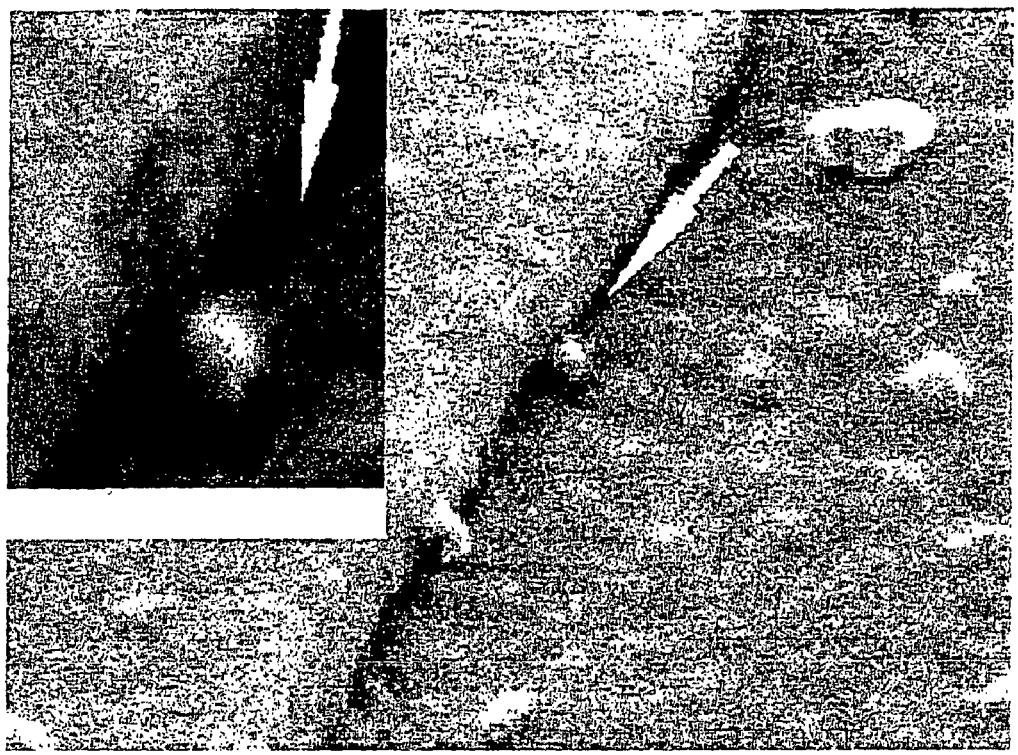
FIG. 3 is an SEM picture of the region between two electrodes according to the method of the invention.

In order to detect the bound oligonucleotides, and to show that they retain their selective self-assembly properties, a solution of biotinylated oligonucleotide X of sequence TCT-TGTTGTTCGCCATCCTG-biotin (complementary to X) was applied to the electrode array for 90 min to allow the biotinylated oligonucleotides to hybridise to the surface-bound oligonucleotide monolayers. Using an anti-biotin antibody detection procedure described below, the presence of the biotin label (and hence the thiolated oligonucleotides) can be detected via a local colour darkening. FIG. 2 shows that this occurs on electrodes 2, 4 and 6 from which the MCH monolayer was removed. We note that the gap between opposing electrodes is too small to be resolved by optical microscopy in FIG. 2 but its presence can be inferred from the colouring of the electrodes and the abrupt change in colour across the designed location of the gap. A SEM picture of the region between electrodes 1 and 4 is shown in FIG. 3; the shortest distance between the electrodes is considerably less than 50 nm. The other electrode pairs were separated by similar sized gaps (not shown).

Figure 4A:
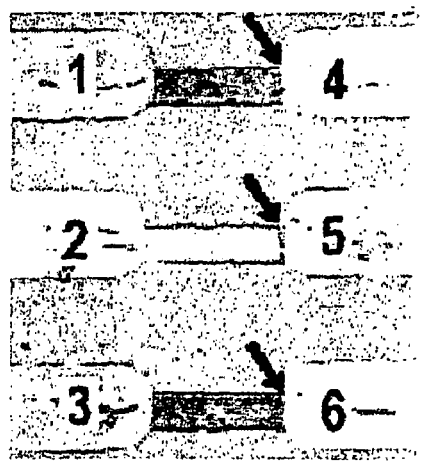
FIG. 4 shows two further electrode arrays coated by the method of the invention.
Figure 4B:
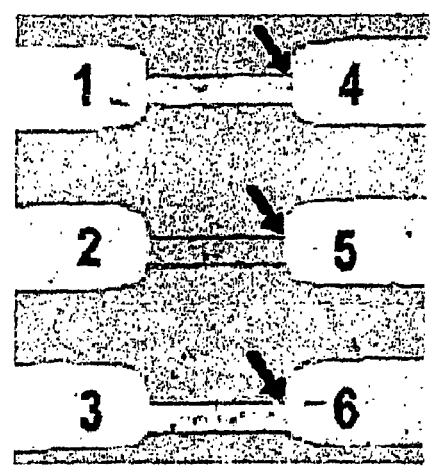

FIG. 4 shows two electrode arrays on which electrodes 1, 3 and 5 were coated with thiolated oligonucleotide Y (AG-GTCGCCGCCC-thiol) and then immersed in 1 mM MCH for 60 min to strengthen the protection capabilities of the oligonucleotide monolayers. Next, the MCH remaining on electrodes 2, 4 and 6 of both arrays was desorbed to allow coating with thiolated oligonucleotide X. This coating step does not significantly affect existing MCH-oligonucleotide monolayers since the exchange rate between two thiolated oligonucleotides of similar length, one of which is bound to a gold surface, is expected to be very small. Subsequently, both arrays were again immersed in 1 mM MCH for 60 min, which does not significantly affect the oligonucleotide densities on electrodes already coated with mixed oligonucleotide monolayers. The arrays were then challenged with different biotinylated oligonucleotides for 90 mins: the array in FIG. 4(a) was challenged with biotinylated oligonucleotide Y (of sequence GGGCGGCGACCT-biotin, complementary to Y), the array in FIG. 4(b) with biotinylated oligonucleotide X. The colour change resulting from subsequent detection with the anti-biotin antibody procedure confirms that the thiolated oligonucleotides X and Y bound to the desired electrodes and demonstrates that this technique can be used to deposit different oligonucleotides selectively onto sub-50 nm-separated electrodes. We note that the anti-biotin antibody detection not only shows that the required coating has been achieved but also that the bound thiolated oligonucleotides, which could act as anchor molecules in nanoassembly applications, remain intact and can still hybridise with their complementary counterparts.

Fabrication of Electrode Array.

The electrode array was fabricated on a Si/SiO$_2$ wafer using a two-step shadow evaporation technique (Philipp, G., Weimann, T., Hinze, P., Burghard, M. & Weis, J., "Shadow evaporation method for fabrication of sub 10 nm gaps between metal electrodes", *Microelectron. Eng.* 46, 157-160 (1999)). In the first step, a series of opposing electrodes of separation 35 μm comprising a 35-nm-thick Au layer on top of a 10 nm adhesive layer of Ni/Cr was created by standard UV photolithography, metal evaporation, and lift-off. In the second step, the wafer was tilted appropriately in the evaporator and 5 nm of Ni/Cr followed by 17 nm of Au was deposited in stripes connecting the opposing electrodes. However, because the wafer was tilted, the edges of the existing electrodes closest to the evaporation source shadowed the surface from the evaporation beam leading to the formation of sub-50-nm sized gaps between opposite electrodes.

DNA Detection

The protocol employed to visualise a specific oligonucleotide monolayer formed on a particular electrode of the arrays is based on a calorimetric detection of oligonucleotide hybridisation. Biotinylated oligonucleotides of sequence complementary to the thiolated oligonucleotides X and Y (X: TCTTGTTGTTCGCCATCCTG-biotin and Y: GGGCGGC-GACCT-biotin) were dissolved in 10 mM tris(hydroxymethyl)aminomethane, 1 mM EDTA (TE solution) and 1 M NaCl to a final concentration of 2.5 µM. The appropriate biotinylated oligonucleotide solution was then applied to the electrode array for 90 min at room temperature to hybridise onto the complementary surface-bound thiolated oligonucleotides. The biotinylated oligonucleotide solution was rinsed off in tris-buffered saline (TBS) and, after several further washing steps, the electrode array was immersed in a 1:1000 dilution of monoclonal anti-biotin antibody conjugated with alealine phosphatase in TBS/Tween 20 for 60 min. Immersing the electrode array in a solution of 5-bromo-4-chloro-3-indolyl phosphate/nitro blue tetrazolium causes a local colour darkening where alkaline phosphatase is present, and therefore where the biotinylated oligonucleotides are hybridised to the electrode array. All oligonucleotides were purchased from MWG Biotech AG; all other reagents were purchased from Sigma.

DETAILED DESCRIPTION OF THE DRAWINGS

FIG. 1: Cyclic voltammograms of a bare Au electrode immediately after cleaning (dashed line), the same electrode after coating with a MCH molecular monolayer (solid line), and after desorbing the MCH monolayer (dotted line). All voltammograms were measured at 62 mV/s in 100 mM phosphate buffer at pH 10 vs. a Ag/AgCl reference electrode and started at −0.4 V. An up and down-sweep is shown for each case.

FIG. 2: Selectively coated electrode array. The sub-50 nm gaps separating opposing electrodes occur at the junction between the wide and narrow electrode features as indicated by the arrows. Electrodes labelled 2, 4 and 6 were coated with oligonucleotide X using the selective desorption technique described and subsequently coloured using the anti-biotin antibody detection scheme described. The colour contrast between the electrodes (electrodes 2, 4 and 6 are significantly darker than electrodes 1, 3 and 5) shows that a very high degree of selective coating has been achieved across the nanometre sized gaps. The narrow central stripes are initially darker than the wide electrodes owing to the metal layer being thinner.

FIG. 3: Scanning electron micrograph (SEM) of the junction region between electrodes 1 and 4, of FIG. 2. The picture was taken after the anti-biotin antibody detection process. The inset is an enlarged view of the central region of the main picture and shows the gap to be significantly less than 50 nm.

FIG. 4: Electrode arrays in which electrodes 1, 3 and 5 are coated with oligonucleotides Y and electrodes 2, 4 and 6 with oligonucleotides X. Arrows indicate the nanoscale gaps separating opposing electrodes. (a) Challenging the array with biotinylated oligonucelotides Y, followed by the anti-biotin antibody detection process, electrodes 1, 3 and 5 darken, confirming the presence of surface-bound oligonucelotides Y.

(b) Challenging the array with biotinylated oligonucleotides X, followed by the anti-biotin-antibody detection process, electrodes 2, 4 and 6 darken, confirming the presence of surface-bound oligonucelotides X.

The invention claimed is:

1. A method of forming coatings of at least two different coating molecules on at least two electrodes, the method comprising:
   (a) providing an array of at least two individually-addressable electrodes,
   (b) allowing a layer of a masking molecule to adsorb onto all electrodes,
   (c) inducing electrochemical desorption of the masking molecule from at least one but not all electrodes to expose a first set of exposed electrodes,
   (d) allowing a first coating molecule to adsorb onto the first set of exposed electrodes, thereby generating a first set of coated electrodes,
   (e) exposing all electrodes, including the first set of coated electrodes, to a masking molecule to allow adsorption of the masking molecule onto all electrodes, including the first set of coated electrodes,
   (f) inducing electrochemical desorption of masking molecule from a second set of electrodes to expose a second set of exposed electrodes,
   (g) allowing a second coating molecule to adsorb onto the second set of exposed electrodes;
   wherein the first coating molecule and the second coating molecule each have a molecular weight greater than or equal to 800 Da; and
   wherein the masking molecule has a molecular weight less than or equal to 500 Da.

2. The method according to claim 1 in which the array comprises at least 10 individually-addressable electrodes.

3. The method according to claim 1 comprising repeating steps (c) to (e) at least 8 times so as to form coatings of at least 10 different coating molecules on at least 10 different sets of electrodes.

4. The method according to claim 1 in which the diameter of each electrode is not more than 50 µm.

5. The method according to claim 1 in which the separation between electrodes is not more than 30 µm.

6. The method according to claim 1 in which the electrodes are metal electrodes and the masking molecules and the coating molecules are thiolated.

7. The method according to claim 1 in which the coating molecules are macromolecules having molecular weight of at least 500.

8. The method according to claim 1 in which the coating molecules are oligonucleotides modified with a functional group capable of adsorbing onto the electrodes.

9. The method according to claim 8 additionally comprising providing nanoparticles functionalised with oligonucleotides complementary to the oligonucleotide coating molecules and allowing the strands to hybridise.

10. The method according to claim 1 in which the coating molecules are polypeptides modified with a functional group capable of adsorbing onto the electrodes.

11. The method according to claim 1 in which step (b), step (d) or both also comprise application of an AC or DC electric field in order to induce orientation of the molecules being adsorbed.

12. The method according to claim 1 comprising controlling the potential of electrodes from which desorption is not required in steps (c), step (f) or both so as to prevent desorption from those electrodes.

13. The method according to claim 1 comprising application of an AC or DC potential to the electrodes onto which adsorption is required in step (b), step (e), step (g) or any combination of these.

14. The method of claim 1, wherein the masking molecule has a molecular weight less than or equal to 200 Da.

15. The method of claim 1, wherein the masking molecule has a molecular weight less than or equal to 150 Da.

16. The method of claim 1, wherein the first coating molecule and the second coating molecule each have a molecular weight greater than or equal to 1000 Da.

17. The method of claim 1, wherein the first coating molecule and the second coating molecule each have a molecular weight greater than or equal to 1500 Da.

18. The method of claim 1, wherein the first coating molecule and the second coating molecule each have a molecular weight greater than or equal to 3000 Da.

19. The method of claim 1, wherein the first coating molecule and the second coating molecule are each oligonucleotides having from 5 to 150 bases.

20. The method of claim 1, wherein the first coating molecule and the second coating molecule are each proteins.

21. The method of claim 1, wherein the first coating molecule and the second coating molecule are each enzymes.

22. The method of claim 1, wherein the masking molecule is 6-mercapto-1-hexanol.

23. The method of claim 1, wherein the first coating molecule is an oligonucleotide of sequence CAGGATGGCGAACAACAAGA-thiol and the masking molecule is 6-mercapto-1-hexanol.

24. The method of claim 1, wherein the first coating molecule is an oligonucleotide of sequence AGGTCGCCGCCC-thiol and the masking molecule is 6-mercapto-1-hexanol.

25. The method of claim 1, wherein the first coating molecule is an oligonucleotide of sequence CAGGATGGCGAACAACAAGA-thiol, the second coating molecule is an oligonucleotide of sequence AGGTCGCCGCCC-thiol, and the masking molecule is 6-mercapto-1-hexanol.

* * * * *